United States Patent
Spitz

(10) Patent No.: US 8,026,087 B2
(45) Date of Patent: Sep. 27, 2011

(54) METHOD OF CONTINUOUSLY PRODUCING ETHANOL AND ELECTRICITY FROM A SUSTAINABLE RENEWABLE BIOMASS FEEDSTOCK

(76) Inventor: Russell W Spitz, Jacksonville, FL (US)

( * ) Notice: Subject to any disclaimer, the term of this patent is extended or adjusted under 35 U.S.C. 154(b) by 0 days.

(21) Appl. No.: 12/565,702

(22) Filed: Sep. 23, 2009

(65) Prior Publication Data

US 2010/0233770 A1    Sep. 16, 2010

(51) Int. Cl.
*C12P 7/06* (2006.01)
*C12P 7/08* (2006.01)
*C12P 7/10* (2006.01)

(52) U.S. Cl. .................... 435/161; 435/163; 435/165

(58) Field of Classification Search .................. None
See application file for complete search history.

(56) References Cited

U.S. PATENT DOCUMENTS 6,605,376 B2 *   8/2003   Verykios ............... 429/401
2003/0196653 A1 * 10/2003   Sanders ................ 127/50

FOREIGN PATENT DOCUMENTS

WO   WO 2008/006384   *  1/2008

OTHER PUBLICATIONS

Paul L. Mask, William C. Morris; "Sweet Sorghum Culture and Syrup Production" ANR-625 Alabama Cooperative Extension System, Nov. 1991, 16 pages.*

* cited by examiner

*Primary Examiner* — Sandra Saucier
*Assistant Examiner* — Thane Underdahl
(74) *Attorney, Agent, or Firm* — Schmid PA

(57) ABSTRACT

Disclosed is a method of continuously producing ethanol and electricity from a sustainable renewable biomass feedstock in a processing plant contiguous to the acreage providing the biomass. The process is a closed loop operation having a dedicated crop grown year round producing multiple crops per acre. The renewable biomass feedstock is a sugar containing feedstock such as sweet sorghum. The biomass is grown year round and produces multiple crops per acre.

14 Claims, 1 Drawing Sheet

Figure 1:
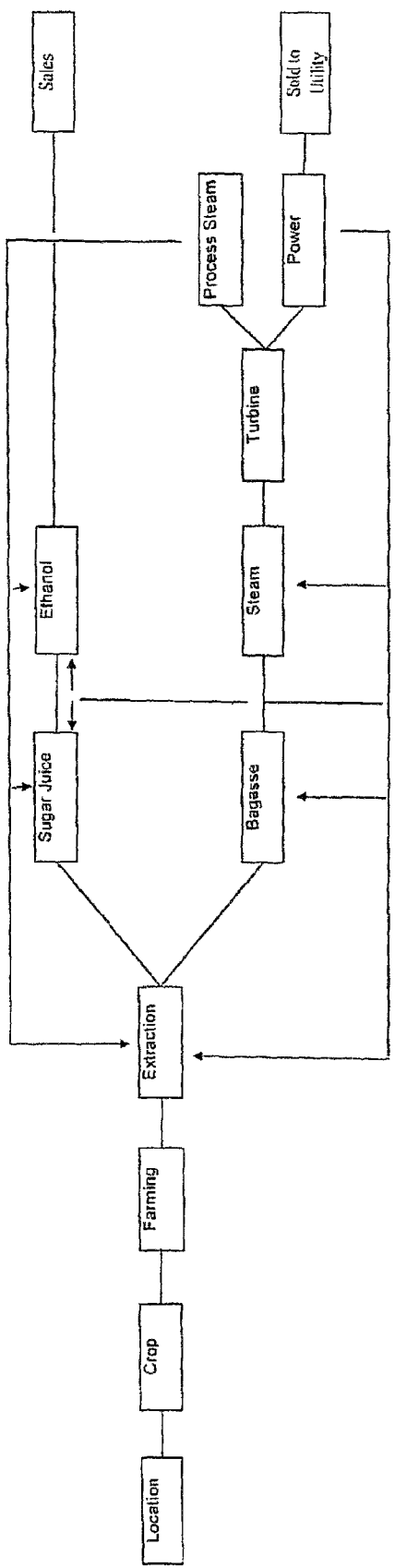

METHOD OF CONTINUOUSLY PRODUCING ETHANOL AND ELECTRICITY FROM A SUSTAINABLE RENEWABLE BIOMASS FEEDSTOCK

FIELD OF THE INVENTION

The present invention generally relates to a method of producing electricity and ethanol from a biomass and in greater detail the method includes harvesting the biomass from contiguous acreage to a processing plant in a year round operation wherein the biomass is sweet sorghum and the ethanol is derived from the extracted sugar juice of the sorghum.

BACKGROUND

The use of biomass as a renewable energy source has been investigated and proposed for many years. Three typical means of using biomass as an energy source include combustion, pyrolysis for the production of gaseous and liquid fuels, and fermentation for the production of ethanol. Sources of biomass can be plants which have certain specific characteristics and which are grown for this purpose, or waste materials from cultivated crops. Significant quantities and sources of biomass can be utilized for the production of energy.

The production of ethanol from biomass is known and is often referred to as "bio-ethanol". The processes for the production of ethanol can be classified into two large categories: those which utilize sugar-containing raw materials—products of energetic cultivations (for example sweet sorghum) and those which utilize cellulosic raw materials originating from energetic cultivations (sorghum, cane, solid residue of sweet sorghum, etc.) as well as from other crop residues. In the first case sugars are directly fermented for the production of ethanol while in the second case a hydrolysis step or other processes are proceeded for the production of sugars which are then converted to ethanol via fermentation.

In regards to the use of sweet sorghum, it is known an energy source with continuing research directed to ethanol production from sorghum materials in the fermentation of extracted sugars. Another ways of using sorghum as a fuel product include the combustion of solid sorghum waste materials. The removal of sugar-containing fluids from sorghum produces considerable quantities of ligno-cellulosic residue, otherwise known as "bagasse". To produce energy, raw sorghum bagasse can be burned as a fuel source.

However, no method is known which can produce excess salable electricity and ethanol derived from a sugar-containing raw material on a continuous year round basis. Furthermore, there is no known method of producing both ethanol and salable electricity economically in a competitive market. Thus, what is needed is a method of producing both ethanol and salable electricity derived from sugar-containing raw materials on a continuous and economical basis.

SUMMARY

The present invention includes a method of continuously producing ethanol and electricity from a biomass feedstock in a processing plant contiguous to the acreage providing the biomass. The biomass is grown year round and produces multiple crops per acre. The contiguous processing plant is energy self sufficient while producing an excess of electricity sold to a utility on a year round basis. Typically, the biomass is sweet sorghum.

In greater detail, there is provided a method of continuously producing ethanol and electricity from a sustainable renewable biomass feedstock using a contiguous acreage. The provided method produces ethanol and electricity from a plant located substantially contiguous with the acreage providing a year round supply of feedstock. The processing plant is energy self sufficient in drying the bagasse and in the fermenting/distilling the sugar juice while producing excess salable electricity.

The biomass feed stock or sweet sorghum is processed after harvested from the contiguous acreage by extracting the sugar juice from the harvested biomass and leaving a bagasse. The bagasse derived from the extracted harvested biomass is dried and gasified to generate steam to drive a steam turbine producing electricity. The sugar juice is both fermented and distilled to produce ethanol using the steam generated by the gasification or combustion of the bagasse. Furthermore, the exhaust from the gasification of the bagasse is used to dry the bagasse. Additionally, a portion of the produced electricity may be used in the method and in this way, combined with the steam and exhaust, the method is self sufficient in its energy needs.

The present method generates both ethanol and excess electricity that may be sold to a utility as electricity produced from a renewable resource and in an embodiment is carbon neutral. The ethanol produced by the method is of course a salable commodity that has many uses including being used as a blended additive in most gasoline products.

The contiguous acreage includes an acreage of at least 25,000 acres or more. In further embodiments the acreage includes of at least 30,000 acres and at least 35,000 acres in a still further embodiment. Typically, the contiguous acreage is at least 35,000 acres. The acreage can be substantially contiguous wherein such interruptions as right of ways, roads or small plots of land or bodies of water disrupt complete contiguousness of the acreage. The contiguous acreage essentially eliminates the need and expense of long hauling the feedstock and its storage.

DRAWINGS

In the Drawings:

FIG. 1 is a flow chart illustrating an embodiment of the method of continuously producing ethanol and electricity from a sustainable renewable biomass feedstock in a processing plant contiguous to the acreage providing the biomass showing the steps of the process.

DETAILED DESCRIPTION

Disclosed is a method of continuously producing ethanol and electricity from a sustainable renewable biomass feedstock in a processing plant contiguous to the acreage providing the biomass. The renewable biomass feedstock is a sugar containing feedstock which is typically sweet sorghum. The biomass is grown year round and produces multiple crops or harvests per acre every year. The contiguous processing plant is energy self sufficient while producing an excess of electricity sold to a utility on a year round basis.

The method includes a closed loop production system having a crop dedicated to a particular processing plant with a sustainable renewable biomass feedstock, typically sweet sorghum, on contiguous acreage to eliminate any feedstock long hauling or storage. The sorghum can be planted and harvested 365 days a year. In an embodiment, the feedstock supplies a centrally located processing plant located within the contiguous acreage to minimize on site hauling of the harvested crop.

In greater detail, the processing plant may in an embodiment extract about 70% sugar juice from the sweet sorghum with the left over stalk (bagasse) is conveyed to a rotary dryer which is heated by the exhaust of the boilers to dry the bagasse from about 51% moisture content to about 42%. After drying the bagasse is gasified (combusted) to produce steam that drives a steam turbine for producing an excess of electricity beyond that needed on site which is sold to the utility. The steam turbine also produces enough steam to provide the site with all the needed process steam which means the site is completely self-sufficient and requires no outside energy.

The continuous method aids in negating the impact of commodity price fluctuations to the feedstock such as that with corn by providing a dedicated acreage for producing the biomass feedstock. The method further provides year round planting and harvesting with substantially no over the road hauling and storage to reduce costs and the environmental impact associated with transporting feedstock. Furthermore in the operation of the system no outside requirement of steam or electric is needed since the method produces the required processing steam and an excess of electricity by incorporating into the method the waste process steam and boiler exhaust.

In detail, the method is continuous in that it can produce electricity and ethanol year round from a crop or biomass feedstock harvested in the substantially contiguous acreage to the processing plant. The biomass feedstock is grown and cultivated year round with at least two crops planted per acre each year. The maturity of the sweet sorghum in a known variety is about 110 days thus it is possible for this variety to produce three crops per year. However, in one embodiment the acreage is left to rest or fallow for a term to replenish the soil.

The amount of contiguous acreage for the method may be in one embodiment at least 25,000 acres and in a further embodiment at least 30,000 acres. In a more preferred embodiment the acreage is at least 35,000 acres. However, the acreage may be more or less in alternative embodiments depending upon the ethanol and electrical output desired and the type of biomass crop grown.

Furthermore, considerations in the location of the acreage include the suitability of the soil, adequate rain fall, such as for example at least 48 inches or more of rain per year and by way of example and not limitation a local having average year round temperatures of at least 70° F. However, it is contemplated in the present system to provide irrigation for the growing biomass crop. Rainfall in most locations is not consistent, wherein the majority of rainfall typically occurs in a single season. Thus, to provide a sustainably consistent harvest of biomass year round the contiguous acreage is typically irrigated to provide the optimum amount of moisture to the growing crop. Additionally, the biomass crop can be fertilized using the vinasse and ash produced in the process.

The term "substantially contiguous" includes contiguous acreage with such interruptions in strict contiguous as right of ways, roads or small plots of land or bodies of water disrupt complete contiguousness of the acreage. The contiguousness of the acreage in relation to itself and the processing plant of the method substantially eliminates feedstock hauling or storage. Thus, in an embodiment the acreage may be interrupted in portions and still be considered substantially contiguous so long as the hauling and storage advantages are retained. The term "crop" means harvests of the biomass feedstock.

The term "processing plant" includes the infrastructure needed to produce the ethanol and electricity of the present method and may include a plurality of structures. The processing plant is energy self sufficient in the drying of the biomass and in the fermentation and distillation of the sugar juice. The processing plant is in an embodiment centrally located within the contiguous acreage. Additionally, in an embodiment the processing plant is typically located near a power transmission line of sufficient capacity to accept the excess electricity produced and sold in the method.

The term "biomass feedstock" includes all biomass materials capable of producing ethanol. For example, cellulosic plants may be used wherein the sugars are extracted by the hydrolysis of complex carbohydrates locked within the cellulose. Additionally, grains may be used such as corn wherein starch within the grain is converted to sugar. The hydrolysis of the carbohydrates can be accomplished using chemical or enzymatic hydrolysis or a combination of both. The sugars in cellulose and hemicellulose are locked in complex carbohydrates. Hydrolysis can simply be understood as a mechanism for unlocking the simple sugars of the monosaccharides of the polysaccharides locked in the cellulose.

Cellulosic biomass is composed of cellulose, hemicellulose and lignin, with smaller amounts of proteins, lipids and ash. Roughly, two-thirds of the dry mass of cellulosic materials are present as cellulose and hemicellulose. Lignin makes up the bulk of the remaining dry mass. Switchgrass may serve as the biomass feedstock to produce a cellulosic ethanol wherein an enzyme is required to breakdown the cellulose into sugar.

In the step of extracting sugar from the biomass, the step includes not only simple sugar juice extraction from such crops as sweet sorghum but also the hydrolysis of complex carbohydrates extracting sugars from the biomass. Typically sugars are extracted through enzymatic reactions converting the cellulose/starches to sugars which are then fermented and distilled into ethanol. The step of extracting sugar includes extraction through hydrolysis of the carbohydrates locked within the cellulose.

The term "bagasse" while meaning the fibrous residue remaining after the sugar containing plants are crushed to extract their juice is further defined herein in an embodiment to mean other plant based materials that can be burned to produce stream. Such is especially true when cellulosic biomass crops are used. For example, in the use of switchgrass only a portion of the biomass is enzymatically converted to sugar with the remaining residue cellulose/lignin or bagasse is then combusted or gasified to produce steam. Furthermore, when the fields are left fallow the crops grown to recharge the soil can be harvested and gasified to produce steam.

The biomass feedstock is processed after being harvested from the contiguous acreage by extracting the sugar juice from the harvested biomass and leaving a bagasse. In the production of alcohol from sweet sorghum and the extraction of the sugar juice a diffuser system is used to maximize yields and reduce power consumption. Other methods may also be used in further embodiments such as crushing the stems or stalks using commercially available cane crushers that may by two roller, three roller, five roller crushers or modern equipment to grind the stalks and extract the juice.

The fermentation and distilling of the sugar juice extracted from the feed stock into ethanol can be accomplish using most any known means within the art. However, the present method provides the energy needed to be self contained. The sugar juice is both fermented and distilled to produce ethanol using the steam generated by the gasification or combustion of the bagasse. In addition to the steam, the portion of the electric power generated in the method is also used internally.

Electricity is produced by the gasification of the bagasse or combustion of the dried bagasse. The bagasse is burned to generate heat to create steam using such known means as boilers to drive a steam turbine to generate electricity. For example, in one embodiment, the method may further include multiple and redundant units with a minimum 50% redundancy for 8,000 hours a year for operation. The feed water is also filtered. Additionally, in an embodiment the steam may be at 900 psi at about 950° F. upon input 60 MW and 360,000 lbs/H process steam output. The turbine and electrical generation is set to run in an embodiment for 364 days and nights for 24 hour operation. The term "continuous" in the process contemplates and includes in the definition the occasional plant shutdown for maintenance and/or repair.

The present method generates both ethanol and excess electricity sold to a utility as electricity produced from a renewable resource and in an embodiment is carbon neutral. The term "utility" includes any entity purchasing the produced excess electricity not used in the process. The term "carbon neutral" used herein refers to the process capturing carbon in the growth of the biomass and then releasing that same captured carbon to a degree in the production of the electricity and ethanol. Of course not all the carbon is released since some is retained in the ethanol and burned bagasse.

Turning now to FIG. 1, an embodiment of the method is illustrated in a flow chart. Within the method, a location for the process method is chosen based in part upon the criteria listed herein for the contiguous acreage and the conditions needed for growing multiple crops of sweet sorghum on the acreage. The crop is cultivated and harvested in an embodiment in a rotational manner so that feedstock is always available for the method year round for continuous operation.

After the harvesting of the crop or biomass the feedstock is processed and the sugar juice is extracted from the feedstock leaving bagasse which is further processed by drying and gasification. Steam is generated in the gasification of the bagasse to drive a turbine to generate electricity which is sold to a utility. The utility can be any entity which purchases the electricity. A portion of the electricity is used in the process to provide power such that the process is self contained and self sufficient in its energy needs. The excess steam is used in the extraction and distillation/fermentation of the sugar juice in the production of the ethanol. The produced ethanol may then be sold as a market commodity.

While Applicants have set forth embodiments as illustrated and described above, it is recognized that variations may be made with respect to disclosed embodiments. Therefore, while the invention has been disclosed in various forms only, it will be obvious to those skilled in the art that many additions, deletions and modifications can be made without departing from the spirit and scope of this invention, and no undue limits should be imposed except as set forth in the following claims.

The invention claimed is:

1. A method of continuously producing ethanol and electricity from a sustainable, renewable biomass feedstock in a processing plant comprising:
a) harvesting a bagasse containing biomass grown year round from a substantially contiguous acreage of at least 25,000 acres and transporting the biomass to the processing plant;
b) extracting a sugar juice from the harvested biomass while producing moist bagasse;
c) either directly burning the bagasse or gasifying the bagasse then burning the resulting gas to boil water to make steam and an exhaust gas;
d) using the steam to drive a turbine to produce all the electricity necessary for the processing plant and an excess which is sold;
e) recycling the exhaust gas from the bagasse gasification or combustion to dry the bagasse after step b);
f) fermenting the sugar juice to produce a fermentate and distilling the fermentate to produce ethanol.

2. The method of claim 1, wherein the harvested bagasse containing biomass is sweet sorghum.

3. The method of claim 1, wherein the extracting step b) further includes hydrolysis of carbohydrates from the biomass.

4. The method of claim 1, wherein the processing plant is centrally located inside the substantially contiguous acreage.

5. The method of claim 1, wherein the steam is also used to ferment the extracted sugar juice and to distill the ethanol.

6. The method of claim 1, wherein at least two crops of the harvested biomass are produced yearly per acre.

7. A method of continuously producing ethanol and electricity from a sustainable renewable biomass feedstock comprising sweet sorghum in a processing plant comprising:
a) harvesting a bagasse containing biomass comprising sweet sorghum grown year round from a substantially contiguous acreage of at least 25,000 acres and transporting the biomass to the processing plant;
b) extracting a sugar juice from the harvested biomass while producing moist bagasse;
c) either directly burning the bagasse or gasifying the bagasse then burning the resulting gas to boil water to make steam and a exhaust gas;
d) using the steam to drive a turbine to produce all the electricity necessary for the processing plant and an excess which is sold;
e) recycling the exhaust gas from the bagasse gasification or combustion to dry the bagasse after step b);
f) fermenting the sugar juice to produce a fermentate and distilling the fermentate to produce ethanol.

8. The method of claim 7, wherein the extracting step b) further includes hydrolysis of carbohydrates from the biomass.

9. The method of claim 7, wherein the contiguous acreage is at least 30,000 acres.

10. The method of claim 7, wherein the plant is centrally located inside the substantially contiguous acreage.

11. The method of claim 7, wherein the steam is also used to ferment the extracted sugar juice and to distill the ethanol.

12. The method of claim 7, wherein at least two crops of the harvested biomass are produced yearly per acre.

13. A method of continuously producing ethanol and electricity from sweet sorghum in a processing plant comprising:
a) harvesting sweet sorghum grown year round on a substantially contiguous acreage of at least 25,000 acres and transporting the biomass to the processing plant that is centrally located inside the substantially contiguous acreage;
b) extracting a sugar juice from the harvested sweet sorghum while producing moist bagasse;
c) either directly burning the bagasse or gasifying the bagasse then burning the resulting gas to make steam and a exhaust gas;
d) using the steam to drive a turbine to produce all the electricity necessary for the processing plant and an excess which is sold;

e) recycling the exhaust gas from the bagasse gasification or combustion to dry the bagasse after step b);

f) fermenting the sugar juice to produce a fermentate and distilling the fermentate to produce ethanol.

14. The method of claim 13, wherein the contiguous acreage is at least 35,000 acres.

* * * * *